United States Patent [19]

Müller-Rees et al.

[11] Patent Number: 5,362,315
[45] Date of Patent: Nov. 8, 1994

[54] PIGMENTS WHOSE COLOR DEPENDS ON THE VIEWING ANGLE, THEIR PREPARATION AND USE

[75] Inventors: Christoph Müller-Rees, Pullach; Robert Maurer; Jürgen Stohrer, both of München; Franz-Heinrich Kreuzer, Martinsried; Silvia Jung, München; Franz Csellich, Unterhaching, all of Germany

[73] Assignee: Consortium für elektrochemische Industrie GmbH, Munich, Germany

[21] Appl. No.: 155,353

[22] Filed: Nov. 22, 1993

[30] Foreign Application Priority Data

Dec. 3, 1992 [DE] Germany .............. 4240743

[51] Int. Cl.⁵ .................. C09K 19/54; C09K 19/02
[52] U.S. Cl. ................... 106/493; 106/499; 106/500; 106/505; 106/506; 252/299.5; 528/502
[58] Field of Search ............. 106/493, 499, 500, 505, 106/506; 528/502; 252/299.5

[56] References Cited

U.S. PATENT DOCUMENTS

| 4,388,453 | 6/1983 | Finkelmann et al. ............ 528/15 |
| 4,410,570 | 10/1983 | Kreuzer et al. .............. 427/374.1 |
| 4,780,383 | 10/1988 | Garrett et al. ............... 430/11 |
| 5,211,877 | 5/1993 | Andrejewski et al. .......... 252/299.1 |

FOREIGN PATENT DOCUMENTS

| 0066137 | 7/1985 | European Pat. Off. . |
| 0358208 | 3/1990 | European Pat. Off. . |
| 0383376 | 8/1990 | European Pat. Off. . |
| 3110048 | 9/1982 | Germany . |
| 3604757 | 12/1987 | Germany . |

OTHER PUBLICATIONS

Ullmanns Encyclopädie d. technischen Chemie, 4th edition, 1976, vol. 18, pp. 631–634 no month.
D. J. Broer et al. in 14th Int. Liquid Conf., Abstracts II, 921 (1992) no month "Density crosslinked cholesteric polymer networks".
CA 113(22):201523y May 1990 of JP 02-131223.
CA112(18):169216s of EP 89-105 729 Mar. 1989.
CA112(16):149138q of DE 3909704 Oct. 1989.
CA112(4):21552c, "Orientational Order in Thin Layers of Thermotropic Comb-Like Polymer", Geschke, D. et al., Makromol. Chem. Rapid Comm. 10(1) 595-9, 1989 no month.
CA111(16):144258y of JP 01-062616, Mar. 1989.
CA111(4):24780r "Stress-Optical & Thermochemical Measurements on Liquid-Crystalline Elastomers", Hammerschmidt, K. et al., Makromol. Chem. 190(5), 1089-1101, 1989 no month.
C. G. Roffey, Photopolymerization of Surface Coatings, (1982) John Willey & Sons Chichester, pp. 137-208, "Photopolymerizable film-forming materials".
De Visser et al., J. Polym. Sci. A1 (9), p. 1894, (1971) no month "Monomer Preparation and Characterization".
P. J. Shannon et al., Macromolecules, 1984, 17, 1873-1876 no month "Photopolymerization in Cholesteric Mesophases".
CA113(14):124523u of US 4867538 Sep. 1989.
Molecular Crystals and Liquid Crystals, Letters, vol. 123, No. 1 /4, no month 1985, pp. 347-353, D. Makow "Color Gamut of Liquid Crystal Polysiloxanes".
Conference Record of the 1991 International Display Research Conference (Cat. No. 91CH3071-8), San Diego, Calif., USA, 15-17 Oct. 1991 pp. 57-59.
Häberle N et al "Right and left circular polarizing color filters made from crosslinkable cholesteric LC-silicones".

Primary Examiner—Karl Group
Assistant Examiner—Scott L. Hertzog
Attorney, Agent, or Firm—Martin Connaughton

[57] ABSTRACT

The invention relates to pigments whose color depends on the viewing angle, their preparation and use.

These pigments comprise oriented three-dimensionally crosslinked substances of liquid-crystalline structure having a chiral phase and, if desired, further dyes and pigments, the further dyes and pigments if present not serving as base for the oriented three-dimensionally crosslinked liquid-crystalline substances having a chiral phase.

11 Claims, 1 Drawing Sheet

PIGMENTS WHOSE COLOR DEPENDS ON THE VIEWING ANGLE, THEIR PREPARATION AND USE

FIELD OF INVENTION

The invention relates to pigments whose color depends on the viewing angle, their preparation and use.

BACKGROUND OF INVENTION

The most widely used prior art pigments consist of particles which absorb a portion of the incoming light and reflect the remainder. The reflected portion of the light determines the color impression.

In addition there are pigments whose color is due to interference effects. These pigments are known as pearl luster pigments. They consist of a base material, most frequently mica platelets, to which thin layers of substances having different optical densities have been applied. These layers often consist of heavy metal compounds (Ullmanns Encyclopädie der technischen Chemie, 4th edition, 1976, Volume 18, p. 631–634). The application of pearl luster pigments containing heavy metals is problematic for reasons of environmental pollution during processing and disposal.

EP-A 383,376 describes the use of cholesteric liquid crystals instead of heavy metal compounds for coating mica platelets and other organic and inorganic base materials. While it is true that the use of cholesteric liquid crystals avoids the disadvantage of coatings containing heavy metals, the base materials themselves often contain heavy metals. Moreover, the above mentioned pigments must be able to meet processing and application parameters. For example, the base material must not exceed a particular thickness otherwise the preparation of finely divided pigments is hampered. It is true that the base materials are very thin in the case where mica or metal flakes are used, but they need to be coated on the front and back in layer thicknesses to be strictly maintained.

SUMMARY OF THE INVENTION

The object of the invention is to provide pigments which avoid the disadvantages of the prior art and make it possible to achieve novel color effects by means of circularly polarized light.

The object is achieved by pigments whose color depends on the viewing angle and comprise oriented three-dimensionally crosslinked substances of liquid-crystalline structure having a chiral phase and, if desired, further dyes and pigments, the further dyes and pigments if present not serving as base for the oriented three-dimensionally crosslinked liquid-crystalline substances having a chiral phase.

For the purposes of the invention, color is not only understood to mean the color impression of the wavelength region of visible light perceivable by the human eye but also the color impression of the adjacent UV and IR wavelength regions not perceivable by the human eye but measurable by known instruments, such as UV and IR spectrometers.

In one embodiment, the pigments according to the invention exclusively comprise an interference layer, this interference layer being composed of oriented three-dimensionally crosslinked liquid-crystalline substances having a chiral phase. Accordingly, the color of these pigments resides inclusively in an interference effect. The light reflected by these pigments is circularly polarized.

In another embodiment, the pigments according to the invention contain, in addition to the oriented three-dimensionally crosslinked liquid-crystalline substances having a chiral phase, other dyes or pigments. Suitable dyes are soluble in the unpolymerized starting substances for preparing the pigments according to the invention. Suitable additional pigments are miscible with the unpolymerized starting substances for preparing the pigments according to the invention. In this embodiment, the angle-dependent color effects of the pigments according to the invention have been combined with additional color effects of known pigments and dyes. Additional pigments which are free of heavy metals are particularly suitable. If the pigments according to the invention contain, for example, carbon black, the unreflected portion of the incoming light is absorbed in the pigment. The desired color impression of the pigments is not impaired by background reflection if it occurs.

The pigments according to the invention do not contain any base material to which the oriented three-dimensionally crosslinked liquid-crystalline substances having a chiral phase have been applied.

The pigments according to the invention can be mixed with one another as desired. This makes it possible for the first time to produce any desired color effects varying with the viewing angle by means of liquid-crystalline substances by simple mixing and thus to obtain colors other than pure spectral color by means of liquid-crystalline substances. Thus, by mixing pigments according to the invention, it is possible for the first time to produce, for example, purple hues by means of liquid-crystalline substances.

The pigments according to the invention are obtainable by orienting three-dimensionally crosslinkable liquid-crystalline substances having a chiral phase, optionally admixing further dyes and/or pigments, crosslinking the liquid crystalline substances three-dimensionally and comminuting them to the desired particle size.

The three-dimensionally crosslinkable liquid-crystalline substances having a chiral phase are preferably applied to a backing, crosslinked on this backing and removed from the backing after crosslinking.

Liquid-crystalline substances which are suitable as starting substances for preparing the pigments according to the invention have a twisted structure whose pitch corresponds to the wavelength of light in the region of UV to IR. This structure is encountered, for example, in cholesteric liquid crystals. Cholesteric liquid crystals or in general liquid crystalline substances having a chiral phase and a twisted structure of the desired pitch can be obtained from nematic, smectic or discotic structures by adding a chiral substance to them. Type and amount of the chiral substance determine the pitch of the twisted structure and thus the wavelength of the reflected light. The twisting of the structure can be left- or right-handed. In addition, the starting substances must contain groups which can be subjected to condensation polymerization or addition polymerization, at least some of which are present in the form of difunctional, trifunctional or higher functional building blocks. Examples of such groups are methacryloxy and acryloxy groups.

Suitable materials and their preparation are described, for example, in DE-C2-3,604,757, EP-A2-358,208, EP-A0 066 137 (corresponding U.S. Pat. No.

4,388,453, issued on Jun. 14, 1983) or in the references in D. J. Broer et al., in 14. Int. Liquid Conf., Abstracts II, 921 (1992). Three-dimensionally crosslinkable polyorganosiloxanes according to EP-A-358,208 are preferred. In principle, any cholesteric liquid crystals can serve as starting materials for preparing the pigments according to the invention. A single type of cholesteric liquid crystal or a mixture of these liquid crystals can be used. A dye or mixtures of dyes can be used.

In a preferred embodiment, the dye to be used is a pigment. In a further preferred embodiment, the dye to be used in the process according to the invention is soluble in the liquid crystal (mixture) used. In the process according to the invention, an individual pure cholesteric liquid-crystalline substance is preferably used.

Admixing of the pigments and/or dyes to the other starting substances takes place in the usual manner, for example by adding them with stirring. In the pigment according to the invention, admixing of the dyes and/or pigments results in a combination of angle-dependent color effects of the liquid-crystalline substances with the known color effect(s) of the substances admixed in each case. However, admixture of these substances does not change anything in the further process steps for preparing the pigments according to the invention.

The pigment color desired in a particular case may also be obtained by mixing defined liquid crystal base mixtures in suitable weight ratios. In this case, too, the further process steps for preparing the pigments according to the invention are not changed thereby. The further description of the preparation process therefore applies to all variants of the pigments according to the invention.

Liquid crystals containing twisted phases do not develop their optical characteristics until the individual molecules are arranged in layers and are uniformly ordered within a layer. The molecules change their preferred direction from layer to layer, as a result of which helix-like structures are formed. To achieve this, the molecules are oriented by means of known methods, such as, for example, by means of orientation layers or electric or magnetic fields. Such methods are known, for example, from the following references: CA113 (22), 201523y; CA113 (14), 124523u; CA112 (18), 169216s; CA112 (16), 149138q; CA112 (4), 21552c; CA111 (16), 144258y; CA111 (4), 24780r.

To prepare the pigments according to the invention, the starting substances mentioned are oriented in a known manner. This can be accomplished, for example, by knife-coating them onto a backing made of metal, plastic or glass. This backing can have been provided, if desired, with an orientation layer made of, for example, polyimide or polyvinyl alcohol. They may also have been silanized for this purpose. However, it is also possible to shear the starting substance between two sheets. Preferably, one or two polyethylene terephthalate sheets are used.

Knife-coating or liquid-crystalline polyorganosiloxanes onto a sheet is known, for example from EP-A-358,208.

Crosslinking of the oriented liquid-crystalline substances is carried out as disclosed for the material in question from the prior art. Thus, for example, liquid-crystalline polyorganosiloxanes can be crosslinked thermally by the method described in EP-A-66,137. The liquid-crystalline polyorganosiloxanes described in AP-A-358,208 can be crosslinked three-dimensionally by photochemical means, for example by irradiation with UV light. A survey of methods of crosslinking oriented starting materials photochemically can be found in C. G. Roffey, Photopolymerization of Surface Coatings, (1982) John Willey & Sons, Chichester, p. 137–208.

The crosslinked oriented liquid-crystalline substances having a chiral phase are, if desired, removed from the backing. If a sheet is used as the backing, mechanical removal of the brittle crosslinked liquid crystals from the backing can be accomplished, for example, by guiding the backing over a deflecting roller of small diameter. This results in the crosslinked material being peeled off from the sheet. However, any other method by which the polymerized material can be removed from the backing is also suitable.

The oriented three-dimensionally crosslinked support-free liquid-crystalline material is comminuted to the particle size desired in each case. This can be effected, for example, by milling in universal mills. Depending on the desired application of the pigments, particle sizes having a diameter of about 10 mm up to one $\mu$m can be prepared. Preferably the pigments have a particle size of between 5 mm and 5 $\mu$m. The pigments have a thickness of between 1 and 100 $\mu$m, preferably 5 to 50 $\mu$m.

In order to narrow the particle size distribution, the mill base can then be classified, for example by screening.

The pigments according to the invention are suitable for coloring a wide range of materials, such as paints and coatings, plastics, fiber raw materials, cosmetics or printing inks of any type, for example screen printing inks. To this end, the pigments are incorporated in the particular material like known pigments. The corresponding pigment-containing compositions thus prepared exhibit the same coloristic properties described for the pigments themselves.

The invention also relates to compositions containing at least one pigment according to the invention. They are in particular compositions which comprise, apart from the pigments according to the invention at least one substance from the group consisting of phenolic resins, amino resins, alkyd resins, polyvinyl acetate resins, epoxy resins, polyurethane resins, polyethylene resins, chlorinated rubber resins, cyclorubber resins, chlorinated polypropylene, ketone resins, acrylate resins, melamine resins, ureaformaldehyde resins, phenol/-formaldehyde resins or at least one substance from the group comprising acrylonitrile/butadiene/styrene copolymers, cellulose acetate, cellulose acetobutyrate, cellulose acetopropionate, cellulose nitrate, cellulose propionate, casein plastics, polyamide, polycarbonate, polyethylene, polybutylene terephthalate, polymethyl methacrylate, polypropylene, polystyrene, polytetrafluoroethylene, polyvinyl chloride, polyvinylidene chloride, polyurethane, styrene/acrylonitrile copolymers, unsaturated polyester resins.

The above mentioned compositions enable novel color effects to be produced, particularly in combination with smooth curved surfaces. These surfaces appear to be intrinsically differently colored. This different coloring changes depending on the location of the observer.

Compositions according to the invention comprising at least one substance from the group comprising phenolic resins, amino resins, alkyd resins, polyvinyl acetate resins, epoxy resins, polyurethane resins, polyethylene resins, chlorinated rubber resins, cyclorubber resins, chlorinated polypropylene, ketone resins, acrylate resins, melamine resins, ureaformaldehyde resins, phenol/-formaldehyde resins, and about 10% by weight (relative to the total weight) of the pigments according to the invention exhibit, after being applied to a black metal sheet high color brilliance and a varying color impression depending on the viewing angle. The reflected light is circularly polarized. Even if the liquid-crystalline polyorganosiloxane pigment incorporated in the composition is used in particle sizes of less than 25 μm, the high color brilliance and the varying color impression depending on the viewing angle are maintained.

Compositions comprising at least one pigment according to the invention and one substance from the group comprising phenolic resins, amino resins, alkyd resins, polyvinyl acetate resins, epoxy resins, polyurethane resins, polyethylene resins, chlorinated rubber resins, cyclorubber resins, chlorinated polypropylene, ketone resins, acrylate resins, melamine resins, urea/formaldehyde resins, phenol/formaldehyde resins are suitable in particular for coating metallic surfaces. If such compositions are used for coating automobiles, a passing automobile thus coated appears to an observer in various colors. These colors can be adjusted as desired by suitable selection of the pigments used.

The pigments according to the invention are furthermore suitable as security marking. Thus, for example, paints, coatings and sheets containing pigments according to the invention which show reflection in the UV or IR region can be used as markings and security marks invisible to the human eye. They can be detected via polarization or angle dependence of the reflected or transmitted light.

Figure 1:
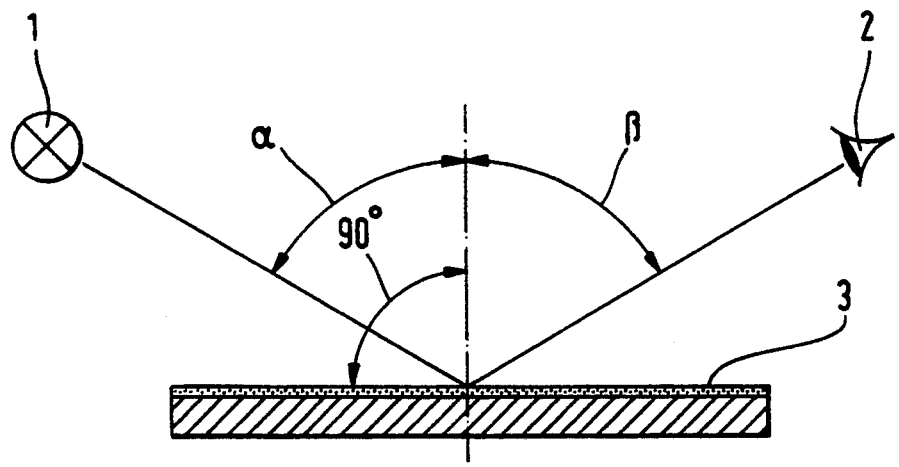
FIG. 1 shows the viewing described in Example 7 of a surface coated with a lacquer containing pigments according to the invention.

In this FIGURE, 1 is the light source; 2 the viewer; 3 the coated surface; α the angle of the incident light, i.e., the angle between the normal surface and the light source; β is the viewing angle, i.e., the angle between the normal surface and the observer.

The examples which follow serve to further illustrate the invention.

EXAMPLE 1

A: Polyorganosiloxanes Having Side Chains Containing Methacrylic Acid

A solution of 233 g of cholesterol 4-(prop-2-en-1-oxy)benzoate (obtainable according to DE-A 3,110,048), 178 g of 4-trimethylsiloxyphenyl 4-(prop-2-en-1-oxy)-benzoate (obtainable according to EP-A-358,208, page 9, section C) and 56.9 g of tetramethylcyclotetrasiloxane in 400 ml of toluene were refluxed in the presence of 24 mg of dicyclopentadieneplatinum dichloride for 1 hour and, after addition of a solution of 1.2 g of NaOH in 50 ml of ethanol, for another 7 hours in order to effect cleavage of the silyl ether. The reaction mixture was concentrated to ⅓ of its volume in a rotary evaporator, 7.5 g of p-toluenesulfonic acid and 154 g of methacrylic anhydride were added, and the mixture was heated at 100° C. for 1 hour. After the volatile components had been distilled off, the residue was reprecipitated twice with methylene chloride/ethanol.

The product had the following physical and thermodynamic data: glass transition temperature: 14° C., clearing point: 141° C.

B. Preparation of a Pigment 4 g of the polyorganosiloxane prepared as described in A were heated to 70° C. and mixed with 0.11 g of 2-methyl-1-[4-(methylthio)phenyl]-2-morpholino-1-propanone (obtainable under the name Irgacure 907 from Ciba Marienberg GmbH, 6140 Bensheim 1) with stirring until a homogeneous mixture was obtained. This gave a viscous liquid crystal (LC) composition having a reddish shimmer. The liquid-crystalline material was knife-coated at 120° C. onto a polyethylene terephthalate sheet (Hoechst AG, Geschäftsbereich Folien, 6200 Wiesbaden 1) in layer thicknesses of 15 μm, during which the sheet was advanced under the fixed knife at a running speed of about 2 m/min. This simultaneously led to orientation of the liquid-crystalline molecules owing to the shearing gradient between knife and sheet, which became visible by red coloring of the liquid crystal layer. This layer was then irradiated using a mercury discharge lamp (80 W/cm) for 5 seconds and thus crosslinked three-dimentionally. The film produced on the sheet was non-tacky and brittle in the heat and the cold. It had a reflection wavelength of 560 nm. (Angle of incidence and viewing angle 45°, see FIG. 1). Mechanical removal of the liquid-crystalline material obtained in this manner from the backing was accomplished by leading the sheet over a deflecting roller 10 cm in diameter, as a result of which the crosslinked material peels off from the support. Milling of the crosslinked, substrate-free material was carried out in a universal mill. Milling of the crosslinked polyorganosiloxanes predominantly present in the form of leaflets for 5 minutes gave a pulverulent fraction. In order to narrow the particle size distribution, the mill base was then subjected to a screening process. To this end, the milled pigments were screened by means of an analytical screen having a mesh size of 100 μm.

EXAMPLE 2

A. Preparation of a Blue Liquid Crystal Mixture

As described in Example 1, 6 g of the polyorganosiloxane were prepared. It was dissolved in 50 ml of toluene. 2.6 g of cholesterol methacrylate (prepared as described in De Visser et al., J. Polym, Sci., A 1(9), 1893 (1971)) and 9 mg of aluminum cupferon (obtainable under the name Q1301 from Wako Chemicals GmbH, 4040 Neuss) were added to the solution. The toluene was then removed at 70° C. in vacuo in a rotary evaporator to give a viscous LC composition having the following physical and thermodynamical data: glass transition temperature: 4° C., clear point: 132° C.

B. Preparation of a Pigment 4 g of the LC composition prepared as described in A were heated to 70° C., and mixed with 0.11 g of 2-methyl-1-(4- methylthio)phenyl)-2-morpholino-1-propanone (obtainable under the name Irgacure 907 from Ciba Marienberg GmbH, 6140 Bensheim 1) with stirring until a homogeneous mixture was obtained. The liquid-crystalline material was further processed as described in Example 1 under B, except it was applied to the sheet at a temperature of 80° C. and crosslinked photochemically. The film produced on the sheet had a reflection wavelength of 400 nm. The pigments had an intensely blue color.

EXAMPLE 3

A. Preparation of a Polymerizable Monomer: 4-Ethylphenyl Methacryloxybenzoate A solution of 16.9 g of 4-ethylphenyl 4-trimethylsilyloxybenzoate (prepared by the procedure in EP-A-358,208, page 9, sec. C) in 15 ml of toluene and 10 ml of ethanol was refluxed for 1 hour and then freed from volatile components by heating at 100° C. for 60 minutes. The remaining 13.3 g of 4-ethylphenyl 4-hydroxybenzoate were dissolved in 15 ml of toluene together with 30 g of methacrylic anhydride and 1.2 g of toluenesulfonic acid, and the mixture was heated at 100° C. for 1 hour. After cooling, the product was precipitated with hexane and recrystallized from ethanol.

B. Preparation of a Red Liquid Crystal Mixture 6 g of the polyorganosiloxane prepared as in Example 1A were dissolved in 50 ml of toluene. 1.5 g of 4-ethylphenyl methacryloxybenzoate (prepared as in Example 3A) and 7.5 mg of aluminum cupferon (obtainable under the name A 1301 from Wako Chemicals GmbH, 4040 Neuss) were added to the solution. The toluene was then removed at 70° C. in vacuo in a rotary evaporator.

This gives a viscous LC composition having the following physical and thermodynamical data: glass transition temperature: −2° C., clearing point: 124° C.

C. Preparation of a Pigment

The mixture thus obtained was treated as described in Example 2B. The film produced on the sheet had a reflection wavelength of 630 nm. The pigments obtained have an intensely red color.

EXAMPLE 4

A. Preparation of a Green Liquid Crystal Mixture 2.8 g of the red-colored mixture (prepared as described in Example 3B), 1.2 g of the blue-colored mixture (prepared as described in Example 2A) and 0.11 g of 2-methyl-1-[4-methylthio)phenyl]-2-morpholino-1-propanone (obtainable under the name Irgacure 907 from Ciba Marienberg GmbH, 6140 Bensheim 1) were mixed with stirring until a homogeneous mixture was obtained. This gives a viscous LC composition having a greenish shimmer and the following thermodynamic data: glass transition temperature: 2° C., clearing point: 128° C.

B. Preparation of a Pigment

The mixture thus obtained was further processed as described in Example 2B by applying it to a sheet at a temperature of 80° C. and crosslinking it photochemically. The film produced on the sheet had a reflection wavelength of 530 nm. The pigments obtained have an intensely green color.

EXAMPLE 5

A. Preparation of a Green Liquid Crystal Mixture

A homogeneous mixture having a green shimmer was prepared from 2 g of cholesterol 11-methacryloxyundecanoate (prepared according to P. J. Shannon et al., Macromolecules, 1984, 17, 1873–1876;) 2 g of cholesterol 4-methacryloxybutyrate (prepared according to P. J. Shannon et al., Macromolecules, 1984, 17, 1873–1876;) and 0.1 g of hexanediol diacrylate (obtainable from Janssen Chimica, 4057 Brüggen 2) by heating to 50° C. and stirring.

B. Preparation of a Pigment

The mixture thus obtained was further processed as described in Example 2B (temperature of the sheet: 30° C.) to give pigments having an intensely green color.

EXAMPLE 6

Preparation of a Pigment Containing Carbon Black 0.2 g of FW1(HCC) carbon black (Degussa, Frankfurt) were incorporated in 10 g of a mixture obtained as in Example 4A with stirring until a homogeneous mixture was obtained. The mixture thus obtained was further processed as described in Example 2B to give pigments having an intensely green color even on a white ground.

EXAMPLE 7

Preparation and Use of a Coating Containing Green Pigments 1 g of the pigment fraction prepared in Example 4 (particle size <100 μm) was dispersed for 5 minuted with stirring in 2 g of thinner (Permacron Supercryl, Verdünnung 3054, Spies and Hecker, 5000 Cologne). This dispersion was added to a mixture of 5 g of a clear coating (Permacron MS Klarlack 8010, Spies and Hecker) and 2.5 g of curing agent (Permacron MS Spezial Härter 3368, Spies and Hecker). The coating formulation thus obtained was evenly sprayed onto a metal sheet provided with a black base (size: 20×25 cm) in the form of fine droplets using a paint spray gun (Sata-Farbspritztechnik GmbH, Ludwigsburg). After coating, the metal sheet was pre-dried at 80° C. for 10 minutes, and a clear coat (coating formulation as described but without pigments) was applied twice as a protective layer.

The resulting metal sheet exhibits a green color of high brilliance at small angles $\alpha$ and $\beta$ (FIG. 1). With increasing angles $\alpha$ and $\beta$, the green color continuously changes to a blue color. Accordingly, on curved surfaces and in the presence of diffuse, non-directional light, a plurality of colors between green and blue are simultaneously visible depending on the viewing angle.

EXAMPLE 8

Preparation and Use of a Coating Containing Mixtures of Pigments According to the Invention 1 g of blue pigment prepared as described in Example 2 and 1 g of red pigment prepared as described in Example 3 were dispersed in 4 g of thinner for 5 minutes with stirring, further processed as described in Example 7, and sprayed onto a metal sheet provided with a black base. The metal sheet was given a clear coat protective layer as described in Example 7. A purple color of high brilliance is observed for small values of $\alpha$ and $\beta$, which with increasing angles $\alpha$ and $\beta$ continuously changes to a turquoise-like color.

EXAMPLE 9

Determination of the Polarization of the Reflected Light

Upon viewing the metal sheet coated according to Example 4 through a polarizer for left circularly polarized or right circularly polarized light, the reflection color is visible in the first case but the metal sheet appears black in the second case.

EXAMPLE 10

Incorporation of Green Pigments in Rigid PVC 90 parts by weight of rigid PVC (obtainable from Wacker-Chemie GmbH, Munich under the name Vinnol H 70 F), 10 parts by weight of bis(2-ethylhexyl) phthalate (Janssen Chimica, 4057 Brüggen 2), 2 parts by weight of Hostastab SnOS 661 (Hoechst AG, Frankfurt), 1 part of partially saponified ester wax obtained from montan acid (Wachs OP; Hoechst AG, Frankfurt) and 10 parts by weight of green pigments from Example 4 were combined and homogenized for 10 minutes at 150° C. and a friction of 1:1.1 using a roll. The resulting composition was processed in a press at 170° C. to give sheets. The sheets exhibit the same green-blue color effects as the coated metal sheet described in the preceding examples.

EXAMPLE 11

Incorporation of Green Pigments in Plasticized PVC 100 parts by weight of plasticized PVC (obtainable from Wacker-Chemie GmbH Munich under the name Vinnol P 70), 50 parts by weight of bis(2-ethylhexyl) phthalate, 1 part of barium/zinc stabilizer (obtainable as Irgastab BZ 505 from Ciba AG, Basle) and 7.5 parts by weight of the green pigments prepared according to Example 4 were combined, homogenized and poured onto a glass plate. After 10 minutes of gelling in a drying cabinet at 180° C., a transparent film is obtained which exhibits an angle-dependent color effect as described in the preceding examples.

What is claimed is:

1. A pigment whose color depends on the viewing angle, which comprises oriented three-dimensionally crosslinked support-free substances of liquid-crystalline structure having a chiral phase and, optionally dyes and pigments, wherein said optional dyes and pigments do not serve as a base for the oriented three-dimensionally crosslinked liquid-crystalline substances having a chiral phase.

2. A pigment as claimed in claim 1, wherein the oriented three-dimensionally crosslinked substances of liquid-crystalline structure having a chiral phase are organosiloxanes in which the number of polymerizable groups is at least two.

3. A pigment as claimed in claim 2, wherein the oriented three-dimensionally crosslinked substances of liquid-crystalline structure having a chiral phase, consists of a mixture of organosiloxanes.

4. A pigment as claimed in claim 1, which contains carbon black as the optional pigment.

5. A process for preparing a pigment as claimed in claim 1, which comprises orienting three-dimensionally crosslinkable substances of liquid-crystalline structure having a chiral phase, optionally admixing further pigments and/or dyes, crosslinking the liquid crystalline structure three-dimensionally and comminuting to the desired particle size.

6. A pigment as claimed in claim 1, wherein the pigment has a thickness of 1 to 100 μm and a diameter of 1 to 10,000 μm.

7. The process as claimed in claim 5, wherein the substances, for orientation, are applied to a backing and again removed therefrom before comminution.

8. A pigment as claimed in claim 1, further having at least one substance from the group consisting of phenolic resins, amino resins, alkyd resins, polyvinyl acetate resins, epoxy resins, polyurethane resins, polyethylene resins, chlorinated rubber resins, cyclorubber resins, chlorinated polypropylene, ketone resins, acrylate resins, melamine resins, urea/formaldehyde resins, and phenol/formaldehyde resins.

9. A pigment as claimed in claim 1 further having at least one substance from the group consisting of acrylonitrile/butadiene/styrene copolymers, cellulose acetate, cellulose acetobutyrate, cellulose acetopropionate, cellulose nitrate, cellulose propionate, casein plastics, polyamide, polycarbonate, polyethylene, polybutylene terephthalate, polymethyl methacrylate, polypropylene, polystyrene, polytetrafluoroethylene, polyvinyl chloride, polyvinylidene chloride, polyurethane, styrene/acrylonitrile copolymers and unsaturated polyester resins.

10. Pigmented paints, coatings, plastics, fiber raw materials, printing inks and cosmetics comprising a pigment as claimed in claim 1.

11. A security marking wherein the marking comprises a pigment as claimed in claim 1.

* * * * *